United States Patent [19]

Yamamoto et al.

[11] 4,002,755
[45] Jan. 11, 1977

[54] TRIAZOLOQUINAZOLINES

[75] Inventors: Michihiro Yamamoto; Shigeaki Morooka; Masao Koshiba, all of Nishinomiya; Shigeho Inaba, Takarazuka; Hisao Yamamoto, Kobe, all of Japan

[73] Assignee: Sumitomo Chemical Company, Limited, Osaka, Japan

[22] Filed: Feb. 25, 1975

[21] Appl. No.: 552,889

[30] Foreign Application Priority Data

Feb. 27, 1974 Japan .......................... 49-24621

[52] U.S. Cl. .................. 424/251; 260/256.4 F; 260/256.4 Q
[51] Int. Cl.² ...................................... C07D 487/04
[58] Field of Search ............. 260/256.4 F; 424/251

[56] References Cited

UNITED STATES PATENTS 3,313,815  4/1967  Wolfe et al. ................ 260/256.4 F
3,838,126  9/1974  Wagner ........................ 260/256.4 F

OTHER PUBLICATIONS

Young et al., "Arch. Int. Pharmacodyn", vol. 212, 1974, pp. 205–213.
Naqui et al., "Tetrahedron Letters", No. 25, 1962, pp. 1193–1198.

*Primary Examiner*—Donald G. Daus
*Assistant Examiner*—James H. Turnipseed
*Attorney, Agent, or Firm*—Stevens, Davis, Miller & Mosher

[57] ABSTRACT

Triazoloquinazolines of the formula,

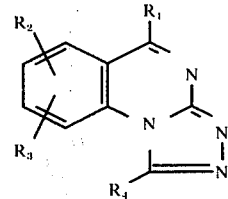

wherein $R_1$ is $C_{1-4}$ alkyl or aryl; $R_2$ and $R_3$ are independently hydrogen, halogen, trifluoromethyl, nitro, $C_{1-4}$ alkyl or $C_{1-4}$ alkoxy, or $R_2$ and $R_3$ together may form methylenedioxy; and $R_4$ is hydrogen, $C_{1-4}$ alkyl, aralkyl, $C_{1-4}$ haloalkyl, or $C_{3-6}$ cycloalkyl; and pharmaceutically acceptable acid addition salts thereof are prepared by (a) reacting a 2-hydrazinoquinazoline derivative with a carboxylic acid or reactive derivative thereof, (b) cyclizing a 2-acylhydrazinoquinazoline derivative with heating or (c) reacting a triazolylbenzophenone derivative with ammonia. Said triazoloquinazolines and pharmaceutically acceptable acid addition salts thereof show excellent anti-inflammatory and analgesic activities.

6 Claims, No Drawings

TRIAZOLOQUINAZOLINES

The present invenion relates to novel triazoloquinazoline derivatives and processes for preparation thereof.

More particularly, the present invention pertains to s-triazolo[4,3-a]quinazoline derivatives of the general formula,

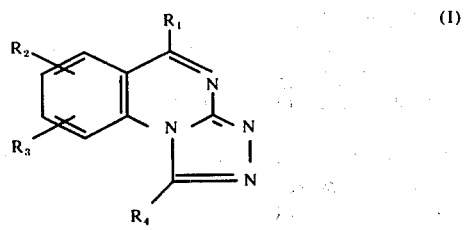

wherein $R_1$ is $C_1-C_4$ alkyl or aryl; $R_2$ and $R_3$ are independently hydrogen, halogen trifluoromethyl, nitro, $C_1-C_4$ alkyl or $C_1-C_4$ alkoxy, or $R_2$ and $R_3$ together may form methylenedioxy; and $R_4$ is hydrogen, $C_1-C_4$ alkyl, aralkyl, $C_1-C_4$ haloalkyl, or $C_3-C_6$ cycloalkyl; and pharmaceutically acceptable acid addition salts thereof, and preparation thereof.

In the definition of the compounds of the general formula (I), the term "alkyl" means both straight- and branched-chain saturated aliphatic hydrocarbon radicals, and the $C_1-C_4$ alkyl may be methyl, ethyl, n-propyl, isopropyl, n-butyl or isobutyl; the term "aryl" includes unsubstituted or substituted phenyl, which may be phenyl, halophenyl, $C_1-C_4$ alkylphenyl or $C_1-C_4$ alkoxyphenyl; the term "halogen" includes, for example, fluorine, chlorine or bromine; the $C_1-C_4$ alkoxy may be methoxy, ethoxy, n-propoxy, isopropoxy or n-butoxy; the term "aralkyl" may be benzyl, phenethyl or halobenzyl; the $C_1-C_4$ haloalkyl may be chloromethyl, dichloromethyl, trichloromethyl, trifluoromethyl, bromomethyl, dibromomethyl, 1-chloroethyl, 2-chloroethyl, 1,1,2,2-tetrafluoroethyl or 1,1,2,2,2-pentafluoroethyl; and the term "cycloalkyl" may be cyclopropyl, cyclobutyl, cyclopentyl or cyclohexyl.

An object of the present invention is to provide novel triazoloquinazoline derivatives of the formula (I). Another object of the present invention is to provide processes for preparing the triazoloquinazoline derivatives of the formula (I). A further object of the present invention is to provide novel hydrazinoquinazoline derivatives of the formula (II) as mentioned below and a process for preparation thereof. A still further object of the present invention is to provide novel acylhydrazinoquinazoline derivatives of the formula (IV) as mentioned below and processes for preparing thereof.

Triazoloquinazoline derivatives represented by the general formula (I), which can be obtained according to the present invention, are novel and have excellent pharmacological properties, particularly anti-inflammatory and analgesic effects, which render them useful as synthetic medicines. Illustratively, 1-methyl-5-phenyl-7-chloro-9-triazolo[4,3-a]quinazoline shows remarkable inhibitory action for carrageenin-induced edema in rat, while no toxic symptoms are observed.

The triazoloquinazoline derivatives of the formula (I) may form acid addition salts by treating with suitable acids, which include inorganic acids such as hydrochloric acid, hydrobromic acid, sulfuric acid and phosphoric acid, and organic acids such as acetic acid, tartaric acid, malonic acid, succinic acid, maleic acid, fumaric acid, citric acid, lactic acid or malic acid. Those pharmaceutically acceptable acid addition salts are also included within the scope of the invention.

According to the present invention the triazoloquinazoline derivatives of the formula (I) may be prepared by the following methods.

One method for synthesis of the compounds of the formula (I), comprises reacting a 2-hydrazinoquinazoline derivative of the formula,

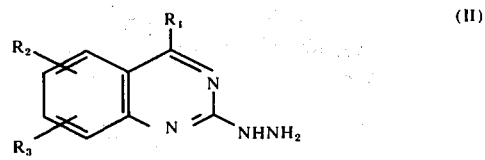

wherein $R_1$, $R_2$ and $R_3$ are as defined above, with a carboxylic acid of the formula, $$R_4-COOH \qquad (III)$$

wherein $R_4$ is as defined above, or its reactive derivative.

Examples of the reactive derivative of the carboxylic acid of the formula (III) include acid anhydrides, acid halides, acid esters, orthoesters of the formula $R_4 - C(OR)_3$ (in which R is $C_1-C_4$ alkyl; and $R_4$ is as defined above) and iminoethers of the formula

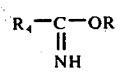

(in which R and $R_4$ are as defined above).

The reaction may be carried out in the presence or absence of a solvent and a condensing agent at room temperature or, if necessary, at elevated temperatures of up to about 250° C.

The solvent may be suitably selected from the organic solvents which are inert to the reactants. Suitable inert solvents are, for example, benzene, toluene, xylene, chlorobenzene, methanol, ethanol, propanol, butanol, methoxyethanol, ethoxyethanol, tetrahydrofuran, dioxane, dichloromethane, chloroform, 1,2-dichloroethane, 1,1,1-trichloroethane, dimethylformamide or acetic acid, and a mixture thereof.

The condensing agent which may be employed as an acid catalyst, may be an inorganic acid such as hydrochloric acid, sulfuric acid, phosphoric acid or polyphosphoric acid, or an organic acid such as acetic acid, methanesulfonic acid or toluenesulfonic acid.

Another method comprises cyclizing a 2-acylhydrazinoquinazoline derivative of the formula,

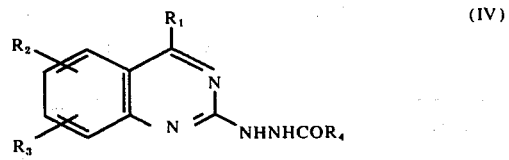

wherein $R_1$, $R_2$, $R_3$ and $R_4$ are as defined above, by heating. The reaction may be carried out at elevated temperatures of up to about 250° C in the presence or absence of a solvent and a condensing agent.

When a solvent is used in the above process, it is suitably selected from the inert organic solvents such as benzene, toluene, xylene, chlorobenzene, nitrobenzene, phenol, ethanol, propanol, butanol, methoxyethanol, ethoxyethanol, pyridine, dimethylformamide, diphenylether, or a mixture thereof.

The condensing agent employed in the reaction may be selected, if necessary, from the group consisting of hydrochloric acid, sulfuric acid, phosphoric acid, polyphosphoric acid, acetic acid, methanesulfonic acid and toluenesulfonic acid.

A further method comprises reacting a triazolylbenzophenone derivative of the formula,

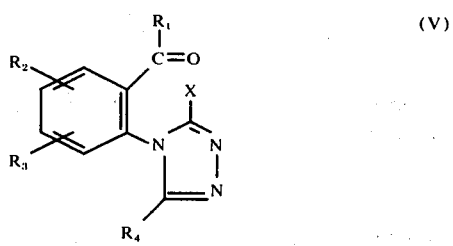

wherein $R_1$, $R_2$, $R_3$ and $R_4$ are as defined above; and X is halogen, mercapto, $C_1$–$C_4$ alkylthio or $C_1$–$C_4$ alkoxy, with ammonia. The reaction may be carried out in the presence or absence of a solvent.

When a solvent is used, suitable solvents are inert solvents such as methanol, ethanol, isopropanol, 2-methoxyethanol, 2-ethoxyethanol, diethyleneglycol, diethyleneglycol dimethylether, toluene, xylene, tetrahydrofuran, dioxane, water, acetonitrile, pyridine, dimethylformamide, dimethylacetamide or dimethylsulfoxide, and a mixture thereof.

Ammonia used in the above process is added into the reaction system as gaseous or liquid ammonia, or as a solution such as methanolic or ethanolic ammonia or ammonia water, or as an ammonia salt such as ammonium acetate, ammonium formate, ammonium succinate or ammonium carbamate, or as an ammono compound such as urea or sodium amide.

The reaction may desirably be accelerated by heating at elevated temperatures.

According to the above processes, the following triazoloquinazoline derivatives and salts thereof can, for example, be obtained:

5-Phenyl-s-triazolo[4,3-a]quinazoline
5-Phenyl-7-chloro-s-triazolo[4,3-a]quinazoline
5-Phenyl-7-nitro-s-triazolo[4,3-a]quinazoline
5-Phenyl-7-methoxy-s-triazolo[4,3-a]quinazoline
5-o-Fluorophenyl-7-chloro-s-triazolo[4,3-a]quinazoline
5-Methyl-s-triazolo[4,3-a]quinazoline
1-Methyl-5-phenyl-s-triazolo[4,3-a]quinazoline
1-Methyl-5-phenyl-7-chloro-s-triazolo[4,3-a]quinazoline
1-Methyl-5-phenyl-7-bromo-s-triazolo[4,3-a]quinazoline
1-Methyl-5-phenyl-7-trifluoromethyl-s-triazolo[4,3-a]quinazoline
1-Methyl-5-phenyl-7-nitro-s-triazolo[4,3-a]quinazoline
1-Methyl-5-phenyl-7-methyl-s-triazolo[4,3-a]quinazoline
1-Methyl-5-phenyl-7-methoxy-s-triazolo[4,3-a]quinazoline
1-Methyl-5-phenyl-7,8-methylenedioxy-s-triazolo[4,3-a]quinazoline
1-Methyl-5-phenyl-9-chloro-s-triazolo[4,3-a]quinazoline
1-Methyl-5-(p-tolyl)-s-triazolo[4,3-a]quinazoline
1-Methyl-5-(o-fluorophenyl)-7-chloro-s-triazolo[4,3-a]quinazoline
1,5-Dimethyl-7-chloro-s-triazolo[4,3-a]quinazoline
1-Ethyl-5-phenyl-7-chloro-s-triazolo[4,3-a]quinazoline
1-Benzyl-5-phenyl-7-chloro-s-triazolo[4,3-a]quinazoline
1-Trifluoromethyl-5-phenyl-7-chloro-s-triazolo[4,3-a]quinazoline
1-(1,1,2,2,2-Pentafluoroethyl)-5-phenyl-7-chloro-s-triazolo[4,3-a]quinazoline
1-Cyclopentyl-5-phenyl-7-chloro-s-triazolo[4,3-a]quinazoline
1-Cyclohexyl-5-phenyl-7-chloro-s-triazolo[4,3-a]quinazoline The 2-hydrazinoquinazoline derivatives represented by the aforesaid formula (II), which are employed as the starting materials of the present invention, include novel compounds and they can be prepared by reacting a quinazoline derivative of the formula,

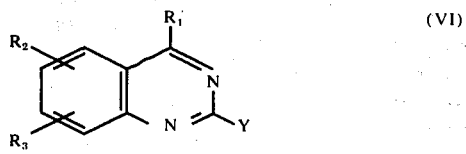

wherein $R_1$, $R_2$ and $R_3$ are as defined above; and Y is halogen, mercapto, $C_1$–$C_4$ alkylthio or amino, or its tautomeric isomer with hydrazine.

The reaction may advantageously be carried out in the presence of a solvent. The solvents preferably employed are, for example, alcohols such as methanol, ethanol, propanol, butanol, methoxyethanol and ethoxyethanol.

The reaction temperature is desirable in the range of from room temperature to the boiling point of the solvent employed.

The 2-hydrazinoquinazoline derivatives thus prepared are used for the subsequent reaction, after isolation by a conventional procedure, or without isolation.

Examples of the 2-hydrazinoquinazoline derivative of the formula (II) obtained by the above process are as follows:

2-Hydrazino-4-phenylquinazoline
2-Hydrazino-4-phenyl-6-chloroquinazoline
2-Hydrazino-4-phenyl-8-chloroquinazoline
2-Hydrazino-4-phenyl-6-trifluoromethylquinazoline
2-Hydrazino-4-phenyl-6-nitroquinazoline
2-Hydrazino-4-phenyl-6-methylquinazoline
2-Hydrazino-4-phenyl-6-methoxyquinazoline
2-Hydrazino-4-phenyl-6,7-methylenedioxyquinazoline
2-Hydrazino-4-(o-fluorophenyl)-6-chloroquinazoline
2-Hydrazino-4-(p-tolyl)-quinazoline
2-Hydrazino-4-methylquinazoline
2-Hydrazino-4-methyl-6-chloroquinazoline The 2-acylhydrazinoquinazoline derivatives represented by the aforesaid formula (IV), which are employed as starting material, are novel compounds. They can easily be obtained by a. reacting a quinazoline derivative of the aforesaid formula (VI), or its tautomeric isomer with an acid hydrazide of the formula,

  (VII)

wherein $R_4$ is as defined above, in the presence of a lower alkyl alcohol such as methanol, ethanol, propanol or butanol, or b. reacting a 2-hydrazinoquinazoline derivatives of the aforesaid formula (II) with a carboxylic acid of the formula (III) or its reactive derivative such as acid anhydride or acid halide, in the presence of an inert solvent such as benzene, toluene, ether, tetrahydrofuran, dioxane, chloroform or 1,2-dichloroethane. Both the reactions (a) and (b) are easily effected at a temperature of from about room temperature to the boiling point of the solvent employed.

Examples of the 2-acylhydrazinoquinazoline derivatives of the formula (IV) obtained by the above processes are as follows:

2-(2-Formylhydrazino)-4-phenylquinazoline
2-(2-Formylhydrazino)-4-phenyl-6-chloroquinazoline
2-(2-Formylhydrazino)-4-phenyl-6-nitroquinazoline
2-(2-Formylhydrazino)-4-phenyl-6-methoxyquinazoline
2-(2-Acetylhydrazino)-4-phenylquinazoline
2-(2-Acetylhydrazino)-4-phenyl-6-chloroquinazoline
2-(2-Acetylhydrazino)-4-phenyl-6-bromoquinazoline
2-(2-Acetylhydrazino)-4-phenyl-6-trifluoromethylquinazoline
2-(2-Acetylhydrazino)-4-phenyl-6-nitroquinazoline
2-(2-Acetylhydrazino)-4-phenyl-6-methylquinazoline
2-(2-Acetylhydrazino)-4-phenyl-6-methoxyquinazoline
2-(2-Acetylhydrazino)-4-phenyl-6,7-methylenedioxyquinazoline
2-(2-Acetylhydrazino)-4-phenyl-8-chloroquinazoline
2-(2-Acetylhydrazino)-4-(p-tolyl)quinazoline
2-(2-Acetylhydrazino)-4-(o-fluorophenyl)-6-chloroquinazoline
2-(2-Acetylhydrazino)-4-methylquinazoline
2-(2-Acetylhydrazino)-4-methyl-6-chloroquinazoline
2-(2-Propionylhydrazino)-4-phenyl-6-chloroquinazoline
2-(2-Phenylacetylhydrazino)-4-phenyl-6-chloroquinazoline
2-(2-Trifluoroacetylhydrazino)-4-phenyl-6-chloroquinazoline
2-(2-Chloroacetylhydrazino)-4-phenyl-6-chloroquinazoline
2-(2-Cyclohexanecarbonylhydrazino)-4-phenyl-6-chloroquinazoline The 2-hydrazinoquinazolines of the formula (II) and the 2-acylhydrazinoquinazolines of the formula (IV) have been found to possess interesting pharmacological properties, particularly anti-inflammatory and antimicrobial activities.

The present invention will be illustrated with reference to the following Examples, which are only given for the purpose of illustration and are not to be interpreted as being limited thereto.

EXAMPLE 1

To a suspension of 1.6 g of 4-phenyl-6-chloro-2(1H)-quinazolinethione in 50 ml of methanol was added 2.0 g of hydrazine hydrate, and the mixture was heated under reflux for 16 hours. The solvent was then removed under reduced pressure and water was added to the residue. The resulting crystals were collected by filtration, washed with water and dried to obtain 1.6 g of yellow product, which was then recrystallized from ethanol to give 2-hydrazino-4-phenyl-6-chloroquinazoline as yellow needles, m.p. 172° – 173° C.

In the next place, to a solution of 1.3 g of 2-hydrazino-4-phenyl-6-chloroquinazoline thus obtained in 100 ml of xylene was added 0.86 g of ethyl orthoacetate, and the mixture was heated under reflux for 2 hours.

After cooling, the separated crystals were collected by filtration and recrystallized from ethanol to give 1-methyl-5-phenyl-7-chloro-s-triazolo[4,3-a]quinazoline as pale yellow crystals, m.p. 335° – 337° C.

EXAMPLE 2

To a suspension of 2.0 g of 2-hydrazino-4-phenyl-6-chloroquinazoline in 50 ml of ethanol were added 5.5 g of ethyl orthoformate and 1 ml of concentrated sulfuric acid. The resulting mixture was stirred at room temperature for 1 hour and then 30 ml of dilute sodium bicarbonate solution was added thereto. The resulting crystals were collected by filtration and recrystallized from ethanol to give 5-phenyl-7-chloro-s-triazolo[4,3-a]quinazoline as colorless needles, m.p. 295° – 297° C.

EXAMPLE 3

To a solution of 9.7 g of 2-chloro-4-phenyl-6-methoxyquinazoline in 300 ml of ethanol were added 15 ml of hydrazine hydrate and 8 ml of glacial acetic acid and the mixture was refluxed for 5 hours. After the precipitate was filtered off, the filtrate was concentrated in vacuo to give crystals. The crystals were collected by filtration, washed with ethanol, and dried to give 7.8 g of 2-hydrazino-4-phenyl-6-methoxyquinazoline, a part of which was recrystallized from ethanol to give yellow scales, m.p. 151° – 152° C.

In the next place, to a solution of 2.0 g of 2-hydrazino-4-phenyl-6-methoxyquinazoline in 100 ml of ethanol were added 3.5 g of ethyl orthoacetate and 0.5 ml of concentrated sulfuric acid. The resulting mixture was refluxed for 3 hours and then the solvent was removed under reduced pressure. To the residue was added ammonia water to basify, and the mixture was extracted with chloroform. The extract was washed with water, dried over anhydrous sodium sulfate and evaporated to dryness in vacuo. To the residue was added ethanol and the crystallized product was collected by filtration, and dried to give 1-methyl-5-phenyl-7-methoxy-s-triazolo[4,3-a]quinazoline as slightly yellow needles, m.p. 251° – 252° C.

EXAMPLE 4

Using a procedure similar to that described in Example 1, there were obtained the following compounds.
1-Methyl-5-phenyl-7-nitro-s-triazolo[4,3-a]quinazoline, m.p. 350° – 352° C.
1-Ethyl-5-phenyl-7-chloro-s-triazolo[4,3-a]quinazoline, m.p. 318° – 319° C.

EXAMPLE 5

To a mixture of 2.72 g of 4-phenyl-6-chloro-2(1H)-quinazolinethione and 2.22 g of acetydrazide was added 100 ml of n-butanol and the mixture was heated under reflux for 20 hours. After cooling, the mixture was poured into 500 ml of water and extracted with ether. The ether extract was washed with water and dried over anhydrous sodium sulfate. The solvent was removed under reduced pressure and the residue was then chromatographed on silica gel using chloroform as an eluent. The product thus obtained was recrystallized from benzene to give 2-(2-acetylhydrazino)-4-phenyl-6-chloroquinazoline, m.p. 227.5° – 228.5° C.

In the next place, 1.1 g of 2-(2-acetylhydrazino)-4-phenyl-6-chloroquinazoline thus obtained was heated at 200° C for 30 minutes. After cooling, the product was recrystallized from ethanol to obtain 1-methyl-5-phenyl-7-chloro-s-triazolo[4,3-a]quinazoline, m.p. 338° – 339° C.

EXAMPLE 6

A mixture of 1.38 g of 2-chloro-4-phenyl-6-chloroquinazoline and 0.74 g of acetydrazide was heated at 220° C for 20 minutes. After cooling, ethanol was added to the mixture and the mixture was filtered to obtain crystals, which were then recrystallized from ethanol to give 1-methyl-5-phenyl-7-chloro-s-triazolo[4,3-a]quinazoline, m.p. 335° – 337° C.

EXAMPLE 7

To a mixture of 2.0 g of 2-chloro-4-phenyl-6-nitroquinazoline and 1.17 g of acetydrazide was added 50 ml of ethanol and the mixture was heated under reflux for 6 hours. After cooling, the separated crystals were filtered, washed with ethanol and dried to obtain pale brown 2-(2-acetylhydrazino)-4-phenyl-6-nitroquinazoline. A part of the product thus obtained was recrystallized from a mixture of ethanol and dimethylformamide to give colorless crystals, m.p. 302° – 303° C (decomp.).

In the next place, a mixture of 0.8 g of 2-(2-acetylhydrazino)-4-phenyl-6-nitroquinazoline thus obtained and 16 g of polyphosphoric acid was heated at 150° to 160° C for 2 hours. The mixture was then poured into ice-water and made alkaline with concentrated ammonia water. The precipitated crystals were filtered, washed with ethanol and then recrystallized from chloroform to obtain 1-methyl-5-phenyl-7-nitro-s-triazolo[4,3-a]quinazoline as pale brown crystals, m.p. 350° – 352° C.

EXAMPLE 8

Using a procedure similar to that described in Example 7, but replacing 2-chloro-4-phenyl-6-nitroquinazoline by 2-chloro-4-phenyl-6-methoxyquinazoline, there was obtained 1-methyl-5-phenyl-7-methoxy-s-triazolo[4,3-a]quinazoline, m.p. 250° – 251° C.

EXAMPLE 9

To a solution of 2.4 g of 2-hydrazino-4-phenyl-6-chloroquinazoline in 50 ml of tetrahydrofuran was added dropwise 2.52 g of trifluoroacetic anhydride and the mixture was stirred at room temperature for 4 hours. Then, the mixture was poured into ice-water and extracted with chloroform. The chloroform extract was washed with a dilute aqueous sodium bicarbonate solution, dried over anhydrous sodium sulfate and the solvent was removed under reduced pressure. The resulting residue was crystallized from isopropyl ether to obtain colorless 2-(2-trifluoroacetylhydrazino)-4-phenyl-6-chloroquinazoline, m.p. 207° – 207.5° C.

In the next place, a mixture of 1.0 g of 2-(2-trifluoroacetylhydrazino)-4-phenyl-6-chloroquinazoline thus obtained and 20 g of polyphosphoric acid was heated at 150° C for 2 hours. The mixture was then poured into ice-water and made alkaline with concentrated ammonia water. The resulting crystals were collected by filtration, washed with water, dried and dissolved in chloroform, and purified by chromatography on silica gel using chloroform as an eluent to give 1-trifluoromethyl-5-phenyl-7-chloro-s-triazolo[4,3-a]quinazoline, m.p. 241° – 242° C.

EXAMPLE 10

To a suspension of 4.5 g of 5-chloro-2-(3-methyl-4H-1,2,4-triazol-4-yl)benzophenone in 450 ml of carbon tetrachloride was added 3.1 g of N-bromosuccinimide and the mixture was heated under reflux for 3 hours. Then, the reaction mixture was filtered and the filtrate was cooled. The resulting crystals were filtered, washed with carbon tetrachloride and dried to obtain 4.3 g of brown 5-chloro-2-(3-methyl-5-bromo-4H-1,2,4-triazol-4-yl)benzophenone. A part of the product thus obtained was recrystallized from ethyl acetate to give colorless needles, m.p. 198° – 199° C.

In the next place, a solution of 0.5 g of the above-mentioned 5-chloro-2-(3-methyl-5-bromo-4H-1,2,4-triazol-4-yl)benzophenone in 20 ml of dimethylsulfoxide was heated, with stirring, at about 180° C for 10 hours, during which ammonia gas was continuously passed into the reaction mixture. After cooling, the reaction mixture was poured into ice-water and the resulting crystals were filtered, washed with water and dried. The crystals thus obtained was dissolved in chloroform and chromatographed on silica gel using chloroform as an eluent. The product thus separated was recrystallized from isopropyl ether to give 1-methyl-5-phenyl-7-chloro-s-triazolo[4,3-a]quinazoline, m.p. 325° – 327° C.

What is claimed is:

1. An s-triazolo[4,3-a]quinazoline of the formula

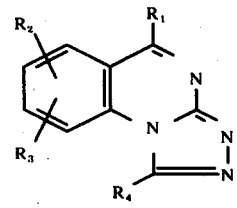

wherein $R_1$ is $C_1$–$C_4$ alkyl, phenyl, halophenyl, $C_1$–$C_4$ alkylphenyl or $C_1$–$C_4$ alkoxyphenyl; $R_2$ and $R_3$ are independently hydrogen, halogen, trifluoromethyl, nitro, $C_1$–$C_4$ alkyl or $C_1$–$C_4$ alkoxy, or $R_2$ and $R_3$ together may form methylenedioxy; and $R_4$ is hydrogen, $C_1$–$C_4$ alkyl, benzyl, phenethyl or halobenzyl; and pharmaceutically acceptable acid addition salts thereof.

2. 1-Methyl-5-phenyl-7-chloro-s-triazolo[4,3-a]quinazoline.
3. 1-Methyl-5-phenyl-7nitro-s-triazolo[4,3-a]quinazoline,
4. 1-Methyl-5-phenyl-7-methoxy-s-triazolo[4,3-a]quinazoline,
5. 1-Trifluoromethyl-5-phenyl-7-chloro-s-triazolo[4,3-a]quinazoline.
6. 5-Phenyl-7-chloro-s-triazolo[4,3-a]quinazoline.

* * * * *